United States Patent
Walker et al.

[11] Patent Number: 5,627,076
[45] Date of Patent: May 6, 1997

[54] METHOD FOR DETERMINATION OF GLYCOLS AND POLYGLYCOLS IN DRILLING FLUID FILTRATES

[75] Inventors: Nyal S. Walker; Patrick L. Henderson, both of Houston, Tex.

[73] Assignee: Baker Hughes Incorporated, Houston, Tex.

[21] Appl. No.: 555,682

[22] Filed: Nov. 13, 1995

[51] Int. Cl.$^6$ .............. G01N 33/24; B01L 9/00; G01J 3/52
[52] U.S. Cl. .............. 436/30; 436/8; 436/60; 436/127; 436/128; 436/165; 436/166; 356/421; 422/104; 422/99
[58] Field of Search .............. 436/8, 25, 30, 436/60, 127, 128, 131, 164, 165, 166, 177; 422/104, 61, 99; 356/421–425

[56] References Cited

U.S. PATENT DOCUMENTS

| | | | |
|---|---|---|---|
| 1,865,472 | 7/1932 | Lamstein | 422/104 X |
| 2,027,816 | 1/1936 | Drucker | 356/423 X |
| 3,436,156 | 4/1969 | Adler et al. | 356/423 |
| 3,882,619 | 5/1975 | Durand et al. | 422/104 X |
| 3,916,157 | 10/1975 | Roulette et al. | 422/104 X |
| 4,073,623 | 2/1978 | Bodart | 356/421 X |
| 4,128,400 | 12/1978 | Mühlböck et al. | 422/104 X |
| 4,751,186 | 6/1988 | Baisch et al. | 422/104 X |
| 4,797,256 | 1/1989 | Watlington, IV | 422/104 X |
| 4,871,258 | 10/1989 | Herpichboehm et al. | 356/422 |
| 4,878,382 | 11/1989 | Jones et al. | 73/153 |
| 4,904,603 | 2/1990 | Jones et al. | 436/30 X |
| 4,938,369 | 7/1990 | Carilli | 422/104 X |
| 5,360,738 | 11/1994 | Jones et al. | 436/30 |

FOREIGN PATENT DOCUMENTS

| | | |
|---|---|---|
| 506261 | 9/1992 | European Pat. Off. . |
| 4-252951 | 9/1992 | Japan . |

OTHER PUBLICATIONS

E.G. Brown *Analyst*, 1955, 80, 755–767.
N.T. Crabb et al. *J. Am. Oil Chem. Soc.* 1968, 45, 611–615.
M. S. Baggetl et al. *Textile Research Journal*. 1975, 45, 871–873.
K.W. Petts et al. *Water Research* 1981 15, 129–132.
V.A. Dubovik et al. VINITI 5593-82, 1982.
P. Pitter et al. *Sb. Vys. Sk. Chem. Technol. Praze* 1982, F24, 147–158.

*Primary Examiner*—Arlen Soderquist
*Attorney, Agent, or Firm*—Fishman, Dionne & Cantor

[57] ABSTRACT

An apparatus and method is presented for the determination of water soluble glycols and polyglycols (polyalkoxylates). The apparatus and method are particularly suited for the on-site quantitation of glycols and polyglycols in aqueous drilling fluids.

6 Claims, 3 Drawing Sheets

METHOD FOR DETERMINATION OF GLYCOLS AND POLYGLYCOLS IN DRILLING FLUID FILTRATES

FIELD OF THE INVENTION

This invention relates generally to a method and apparatus for characterizing aqueous drilling fluids. More particularly, this invention relates to a method and apparatus for field determination of glycol and/or polyglycol concentrations in aqueous drilling fluids.

BACKGROUND OF THE INVENTION

The use of a drilling fluid in drilling operations using the rotary drilling method is well known. The drilling fluid functions to lubricate and cool the drill bit, serves as a carrier the cuttings made by the drilling bit in the borehole, and supplies a hydrostatic head on the formation to counterbalance any pressures of liquids or gasses which are encountered in the various strata through which the drill bit passes. It also creates a plastering effect on the wall of the borehole to limit the flow of fluid from the borehole into the formation, leaving the formation in as near a natural state as possible.

Aqueous drilling fluids are preferred at many sites due to their relatively lower cost compared with oil-based drilling fluids or invert emulsion fluids. Conventionally, aqueous drilling fluids comprise fresh or salt water, clay, weighting agents, and other additives such as thinning agents, fluid loss agents, and the like. One common additive is glycols and polyglycols (polyalkoxylates), which serve to enhance lubrication and reduce shale swelling.

During the course of drilling, the level of glycol and/or polyglycol in the drilling fluid may fluctuate due to diffusion or absorption by the formation. Drilling muds are thus tested at least once daily to monitor the condition of the mud and establish a basis for future recommendations to minimize borehole problems, thus assuring that the basic functions of a mud are carried out as expected. Because of their usefulness in drilling fluids, there is a need for an easy, accurate method for monitoring glycol and/or polyglycol levels on site, that is, in the field. Previous methods for such monitoring include total distillation, which is inconvenient and can lead to inaccuracies if not per/brined with precision, and measurement of the mud's refractive index, which can be inaccurate due to the presence of colored materials and other solutes.

A method for testing polyglycol concentration in the laboratory using complexation with cobaltothiocyanate has been described in "Detergent Analysis, a Handbook for Cost-Effective Quality Control," by B. M. Milwidsky and D. M. Gabriel, published by John Wiley and Sons, New York (1982), p. 100. However, this method requires relatively large amounts of dichloromethane and access to a spectrophotometer, making it impracticable for use at a drilling site.

Accordingly, there remains a need for an efficient, easy and accurate method for monitoring glycol and/or polyglycol levels in drilling muds and other borehole fluid media.

SUMMARY OF THE INVENTION

The above-discussed and other problems and deficiencies of the prior art are overcome or alleviated by the apparatus and method of the present invention. In accordance with the present invention, on-site determination of glycol and/or polyglycol concentration in aqueous drilling fluids comprises the steps of filtering the drilling fluid, pipetting an appropriate amount into a vial, mixing with a cobaltothiocyanate colorimetric assay solution, and comparing the color of the resulting solution with standard solutions. The apparatus of the present invention comprises vials, pipette and pipette tips, wipes, colorimetric assay solution and a reading device.

The present invention provides many features and advantages relative to the prior art. For example, this method and apparatus renders the determination of glycol and polyglycol concentration easy to perform in the field, and provides a much higher degree of accuracy than previous methods. In addition, the method is fast, and uses small amounts of material thus minimizing clean up and disposal requirements. The method and apparatus of this invention is also inexpensive to manufacture and use.

The above-discussed and other features and advantages of the present invention will be appreciated and understood by those skilled in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENT

Figure 2:
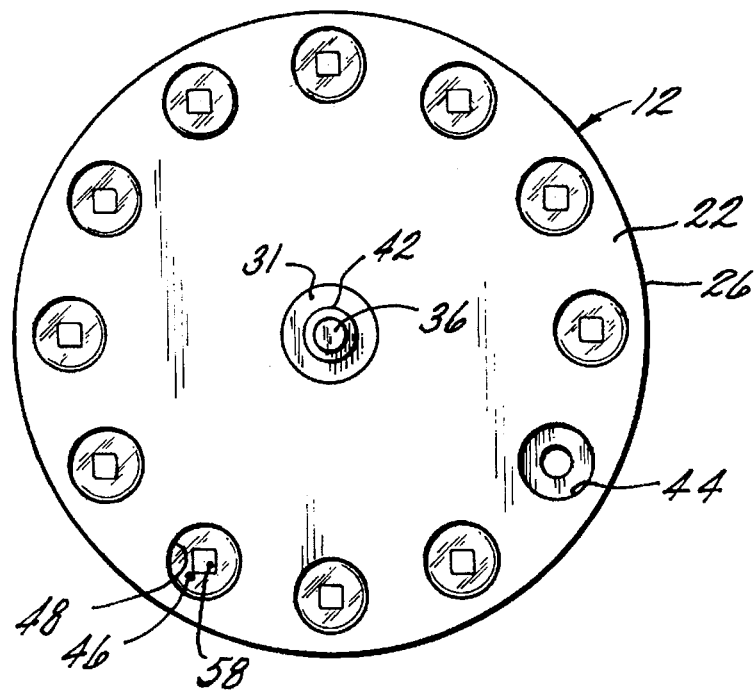
FIG. 2 is a cross-sectional elevation view along the line 2—2 of FIG. 1.

The method of the present invention is based on a colorimetric assay for glycols and/or polyglycols. Although the method is here applied to drilling fluids, it would also be suitable for other fluids containing glycols and/or polyglycols, such as other borehole fluids used, for example, in completion and work-over applications and in waste waters from sewage treatment.

In the first step of the method of this invention, the drilling fluid is passed through an American Petroleum Institute (API) filter press to remove large particulates. It is important that the filtration method have an operating temperature below the cloud point of the glycols and/or polyglycols, so that they remain in solution. For this reason, high temperature high pressure (HTHP) filtration is generally unsuitable.

In the second step, an aliquot of filtrate is volumetrically pipetted into a vial containing a cobaltothiocyanate indicator solution and an immiscible organic solvent. Preferably, the pipette tip is wiped after the aliquot is removed from the filtrate and before it is added to the indicator solution.

The preferred cobaltothiocyanate indicator solution is prepared by dissolving 30 g of cobalt nitrate hexahydrate ($Co(NO_3)_2 \cdot 6H_2O$) with 143 g of ammonium chloride ($NH_4Cl$) and, 256 g of potassium thiocyanate (KSCN) in sufficient water to make one liter. Sixty g of sodium chloride (NaCl) is then added to each kilogram of solution. This indicator solution is suitable for use with water-soluble glycols such as ethylene glycol and propylene glycol, as well as larger polyglycols. In an alternative embodiment, the sodium chloride may be omitted from the indicator solution. Its use is preferred, as it provides more complete extraction of the complexed glycol into the organic solution.

The preferred organic solvent is dichloromethane. However, any suitable organic solvent may be used that titans an immiscible phase with water. Thus, water soluble alcohols, for example ethanol or propanol would be unsuitable A 0.100-mL aliquot of filtrate is preferred because it optimizes the color change over a range from 0 to 5 percent glycol and/or polyglycol (w/w), allowing a 0.5 percent sensitivity. It is difficult for the eye to detect changes in blue color with the required 0.5 percent sensitivity with concentrations of glycol and/or polyglycol greater than 5 percent using an aliquot of 0.100 mL. In order to work above 5 percent, however, the volume of filtrate could be reduced below 0.100 mL and the developed color compared to that of standards prepared using the same reduced volume.

Thus, in the most preferred embodiment,, a 0.100 mL aliquot of filtrate is pipetted into 4.3 g of cobaltothiocyanate indicator solution described above and 4.0 g of dichloromethane. The resulting solution comprises potassium thiocyanate in an amount of about 10.8 percent by weight of the total composition, ammonium chloride in an amount of about 6.0 percent by weight of the total composition, cobalt nitrate hexahydrate in an amount of about 1.3 percent by weight of the total composition, sodium chloride in an amount of about 2.9 percent by weight of the total composition, dichloromethane in an amount of about 48.5 percent of the total composition, and water in an amount of about 30.5 percent by weight of the total composition.

In the next step, the vial is capped and shaken until the aliquot, the cobalt indicator solution and the organic solvent are well-mixed, about one minute by hand. This shaking allows the polyglycols to be extracted into the organic solvent. The vial is then allowed to rest until the water and organic phases have separated.

In the final step, the vial is placed in the reading device (see FIGS. 1–3) and the color of the organic layer is compared to that of standard solutions, thereby indicating the concentration of polyglycols. Alternatively, the color of the test solution may be compared with a color wheel, similar to that contained in, for example, the color wheel for silica determination (based on a molybdenum colorimetric test) marketed by Hach Company, of Loveland, Colo.

The apparatus of the present invention preferably comprises a pipette, pipette tips, wipes, containers, cobaltothiocyanate test solution, and a reading device. Any pipette and tips capable of measuring 0.100 mL with an accuracy of ±0.6 μL is appropriate. Wipes are used to deliver the aliquot volumetrically. Preferably, the containers are capped vials of 8 mL capacity. The cobaltothiocyanate test solution is as described above.

Figure 3:
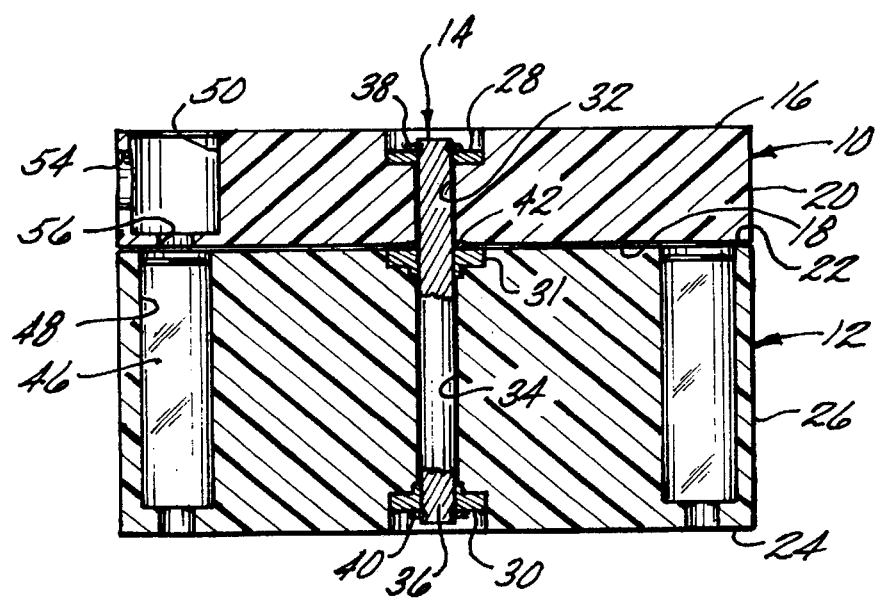
FIG. 3 is a cross-sectional elevation view along the line 3—3 of FIG. 1.
Figure 1:
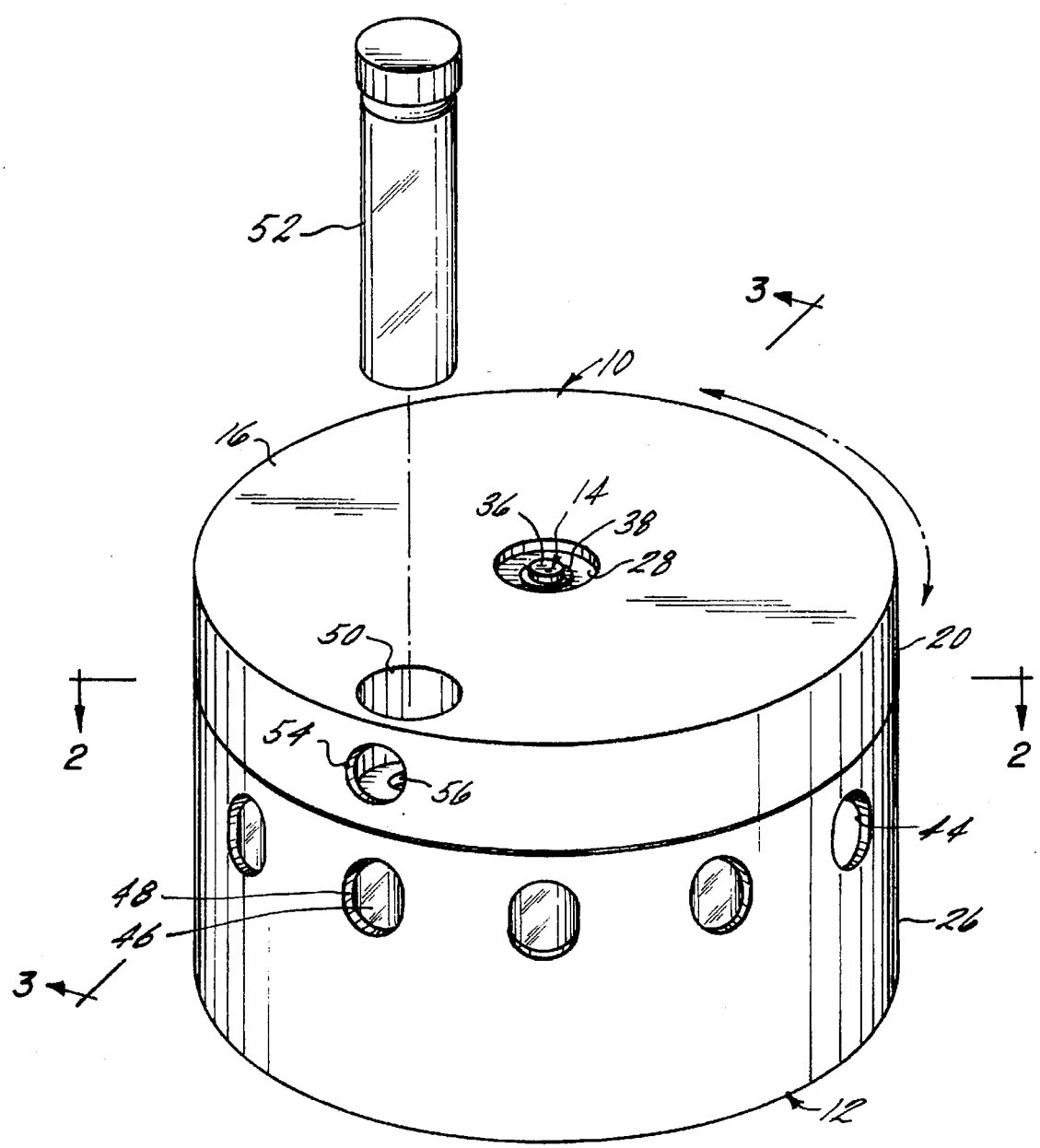
FIG. 1 is a perspective view of the reading device of the present invention.

Referring now to FIGS. 1–3, the reading device of the present invention comprises an upper portion 10 and a lower portion 12, rotatably connected with a suitable connector 14. Upper portion 10 includes a top surface 16, a bottom surface 18 and a cylindrical side surface 20. The lower portion 12 includes a top surface 22, a bottom surface 24, and a cylindrical side surface 26. While a cylindrical shape for the reading device is preferred, any shape allowing physical comparison of the test container with an indicator container is suitable, for example a polygon.

The upper portion 10 and the lower portion 12 are constructed of a material that allows relatively free rotation between the two portions, and that is sufficiently opaque so as to allow comparison of the blue color of the indicator solution without substantial light interference. Suitable materials for the construction of the device include, but are not limited to, opaque materials such as Delrin. To further aid in comparison of the blue indicator color, the interior of the cavities may be lined with a non-reflective material, including but not limited to, white paper.

The connector 14 comprises the following elements. In the center of upper portion 10, and proximate to top surface 16 a boss 28 is located. In the center of lower portion 12 and proximate to bottom surface 24 a second boss 30 is located. In the center of lower portion 12, and proximate to top surface 22 a third boss 31 is located. The first boss 28 is placed within a hollow shaft 32 located in the center of upper portion 10. The second and third bosses 30 and 31 placed within a hollow shaft 34 defined by the inner walls of bottom portion 12. A solid rod 36 is located inside shafts 32 and 34, extending past bosses 28, 30 and 31. Rod 36 is secured in place by E-clip 38, proximate to top surface 16 and E-clip 40 proximate to bottom surface 24. Preferably, a spacer 42 is located on rod 36, between the top surface 22 of the lower portion 12 and the bottom surface 18 of the upper portion 10. Alternatively, the upper portion 10 and the lower portion 12 may be rotatably connected by any suitable means known in the art. Detenters, to control rotation, may be placed on the top surface 22 of the lower portion 12 and the bottom surface 18 of the upper portion 10.

Within the lower portion 12 is at least one cavity 44. The cavity is closed toward the bottom surface 24 of the lower portion 12 and open at the upper surface 22 of the lower portion 12, allowing placement of a container of standard solution 46 therein, perpendicularly to the bottom surface 24 of the lower part 12. At least one port 48 is cut into side wall 26, opening onto the cavity 44, such that a portion of each container 46 within each cavity 44 is visible when viewed from the side of the reading device.

Preferably, each cavity in the bottom part permanently contains containers such as container 46, each container filled with a different standard solution. In an alternative embodiment, the device may be constructed so that the top part may be removed, and the containers within the bottom part may be replaced and/or refilled.

At least one cavity 50 is cut into the tipper portion 10, this cavity being open at the top surface 16 and disposed to accommodate a container of test solution 52. A port 54 is located on the side wall 20 of the upper portion, opening into the cavity 50, thereby allowing a view into a container of standard solution placed in the cavity. Upon rotation of the upper portion 10, the container containing the test solution 52 is aligned with each indicator container 46 in turn, allowing comparison of the colors of each container.

Preferably, at least one opening 56 of approximately 3/16 inch diameter is placed in the bottom surface 18 of the upper portion 10, each opening being located at the bottom of each cavity 50. This opening 56 allows a view onto the top of the containers 46 located in the lower portion 12. A label 58 is placed on the top of each container 46. This label contains the concentration of the standard solution of that particular container. Thus, once a proper color match has been made, by aligning the test solution container 52 with the appropriate standard solution via 46, removing the top container 52 allows the user to look down through the cavity 50 onto the label 56 located on the cap of the standard solution container 46 and determine the concentration of glycol and/or polyglycol of the test solution contained therein. Alternatively, the concentration of the standard solution contained in each container 46 may be labeled on the bottom surface 24 under each container 46, or on the side wall 26 adjacent to each container 46.

Figure 4:
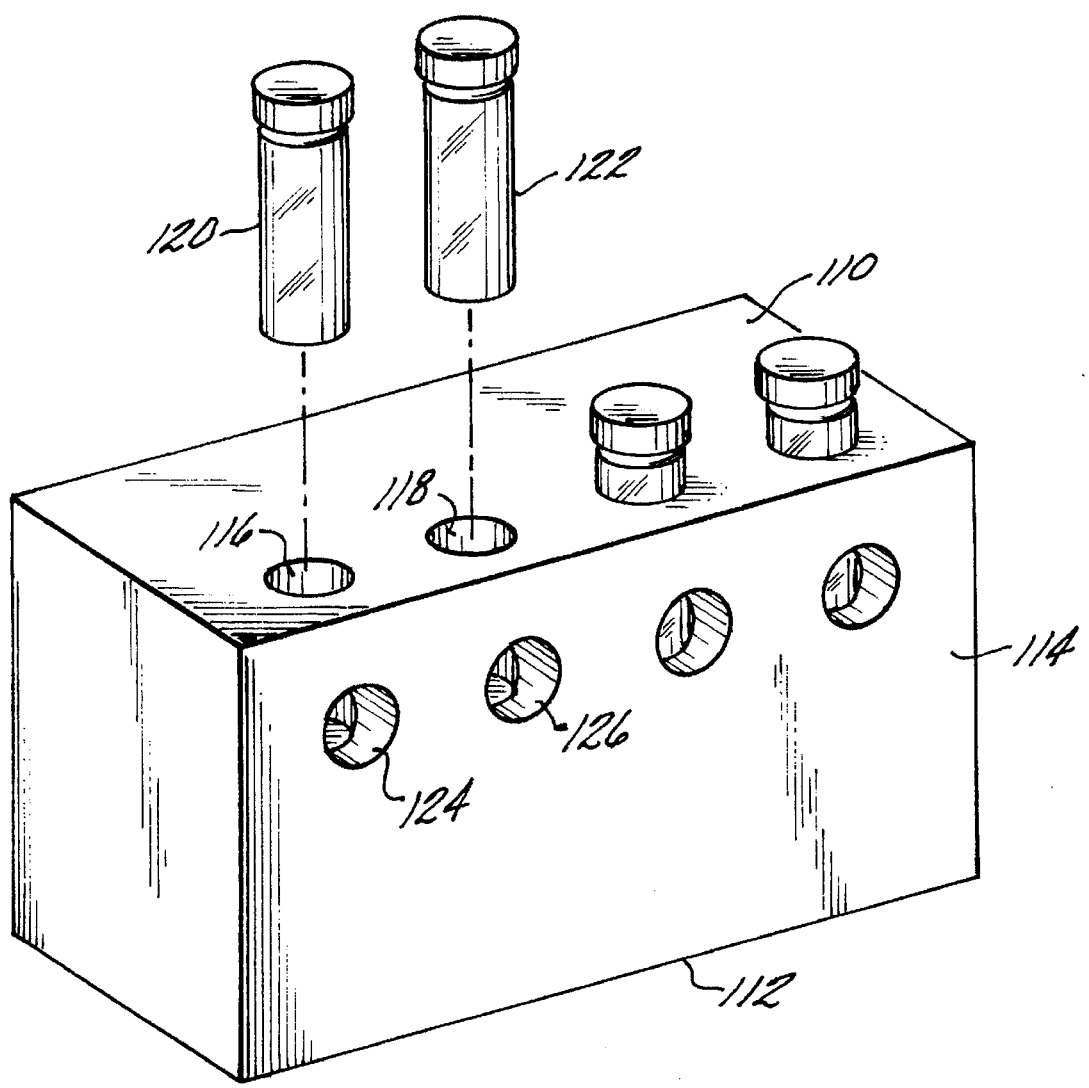
FIG. 4 is a perspective view of an alternative embodiment of the reading device of the present invention.

In an alternative embodiment of the invention (FIG. 4), the reading device comprises a solid structure having a top surface 110, a bottom surface 112 and side walls, including a front side wall 114. The shape formed by the sides of the structure may be cylindrical, square or otherwise polygonal. The structure may comprise any suitable opaque material, including but not limited to styrafoam.

At least two cavities, 116 and 118 are located within the structure, disposed perpendicularly to the bottom surface 112 and open at the top surface 110. The cavities 116 and 118 are each sized so as to hold a container 120 and 122. The cavities may be lined with a suitable non-reflective material, including but not limited to, white paper.

At least two ports, 124 and 126 are located on the front side wall 114, placed so as to allow a view of the bottom portion of each container 120 and 122 within, while blocking a view of the top portion of the container 120 and 122. The container 122, containing a test solution, may be placed within one cavity 116 of the reading device, and compared with the color of the standard solution contained in the second container 122 within the cavity 118. While it is not necessary to block the view of the top portion of the container, it is preferred. The top portion contains the intensely blue aqueous layer of the test solution. Blocking the view of this layer facilitates color comparison of the extracted glycol and/or polyglycol in the lower organic layer.

The method and apparatus described above allows fast, accurate determination of glycols and polyglycols on-site. The test solutions and apparatus are economical. Furthermore, the test is easy to run, and minimizes waste and disposal problems.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A method for determining concentrations of glycols and/or polyglycols in fluids, comprising the steps of:

filtering particulates from the fluid to obtain a filtrate;

mixing an aliquot of the filtrate with a cobaltothiocyanate indicator solution to form a test solution, wherein said cobaltothiocyanate solution comprises cobalt nitrate hexahydrate, ammonium chloride, potassium thiocyanate, water and an immiscible organic solvent;

comparing the resulting color of the test solution with at least one standard cobaltothiocyanate solution to determine the concentration of glycols and/or polyglycols.

2. The method of claim 1 wherein the cobaltothiocyanate solution further comprise sodium chloride.

3. The method of claim 1 wherein said comparison step is accomplished with a reading device.

4. The method of claim 1 wherein said comparison step is accomplished with a hand-held reading device.

5. The method of claim 4 wherein said hand-held reading device comprises an upper portion and a lower portion, said upper portion including a top surface, a bottom surface and a side surface and said lower portion including a top surface, a bottom surface, and a side surface;

connector means whereby said upper portion and said lower portion are rotatably connected;

at least one cavity located in said lower portion, said cavity being closed toward said bottom surface and open at said upper surface, said cavity being sized to allow placement of a container of standard solution therein;

at least one port placed on said side wall of said lower portion, said port opening onto said cavity located in said lower portion, such that at least a part of each container of standard solution within said cavity is visible when viewed from said side wall of said lower portion;

at least one cavity located in said upper portion, said cavity being closed toward said bottom surface and open at said upper surface, said cavity being sized to allow placement of a container of test solution therein;

at least one port placed on said side wall of said upper portion, said port opening onto said cavity located in said upper portion, such that at least the lower part of each container of test solution within said cavity is visible when viewed from said side wall of said upper portion.

6. The method of claim 4 wherein said hand-held reading device comprises:

a structure having a top surface, a bottom surface and side walls, said side walls including a front wall;

at least two cavities located adjacent to each other within said structure, said cavity being closed toward said bottom surface and open at said top surface, and said cavities sized so as to hold containers;

at least two ports, located on said front wall, placed so as to allow a view into said cavities, so that when a container is placed in said cavity, at least the bottom portion of each container is visible.

* * * * *